United States Patent
Onuma

(10) Patent No.: US 9,618,478 B2
(45) Date of Patent: Apr. 11, 2017

(54) SAMPLE ANALYSIS METHOD AND SOLUTION TO BE USED THEREIN

(71) Applicant: ARKRAY, Inc., Kyoto (JP)

(72) Inventor: Naotsugu Onuma, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 232 days.

(21) Appl. No.: 14/156,738

(22) Filed: Jan. 16, 2014

(65) Prior Publication Data

US 2014/0202858 A1 Jul. 24, 2014

(30) Foreign Application Priority Data

Jan. 22, 2013 (JP) ................................. 2013-009469
Jan. 10, 2014 (JP) ................................. 2014-003525

(51) Int. Cl.
*G01N 27/447* (2006.01)
*C07K 1/26* (2006.01)
*B01D 57/02* (2006.01)

(52) U.S. Cl.
CPC ............. *G01N 27/447* (2013.01); *C07K 1/26* (2013.01); *G01N 27/44747* (2013.01); *B01D 57/02* (2013.01)

(58) Field of Classification Search
CPC ........................... G01N 27/44791; C07K 1/26
See application file for complete search history.

(56) References Cited

U.S. PATENT DOCUMENTS

| | | | |
|---|---|---|---|
| 5,192,405 A | 3/1993 | Petersen et al. | |
| 5,599,433 A | 2/1997 | Keo et al. | |
| 8,137,512 B2* | 3/2012 | Tanaka | G01N 27/44756 204/251 |
| 8,361,292 B2* | 1/2013 | Nakayama | G01N 27/44747 204/451 |
| 2006/0102478 A1 | 5/2006 | Robert et al. | |
| 2006/0210994 A1 | 9/2006 | Joyce | |
| 2006/0214104 A1* | 9/2006 | Pope et al. | 250/297 |
| 2008/0124790 A1* | 5/2008 | Yang et al. | 435/287.9 |

(Continued)

FOREIGN PATENT DOCUMENTS

| | | |
|---|---|---|
| CN | 102047104 A | 5/2011 |
| CN | 102128873 A | 7/2011 |

(Continued)

OTHER PUBLICATIONS

Bushey et al. (Journal of Chromatography, 480 (1989) 301-310).*

(Continued)

*Primary Examiner* — Alexander Noguerola
(74) *Attorney, Agent, or Firm* — Morgan, Lewis & Bockius LLP

(57) ABSTRACT

Provided are a sample analysis method using capillary electrophoresis capable of enhancing analysis accuracy, a solution for capillary electrophoresis, and a sample analysis kit. The sample analysis method includes separating and/or detecting a substance to be analyzed in a sample through capillary electrophoresis, in which the substance to be analyzed is separated and/or detected in the presence of a pH buffer substance and a non-surfactant-type zwitterionic substance. Further, the solution for capillary electrophoresis contains a pH buffer substance, a non-surfactant-type zwitterionic substance, and water.

11 Claims, 5 Drawing Sheets

(56) References Cited

U.S. PATENT DOCUMENTS

| | | | |
|---|---|---|---|
| 2010/0006436 A1 | 1/2010 | Oishi et al. | |
| 2010/0032294 A1 | 2/2010 | Nakayama et al. | |
| 2010/0175996 A1* | 7/2010 | Tanaka | G01N 27/44756 204/451 |
| 2010/0258440 A1* | 10/2010 | Sugiyama et al. | 204/451 |
| 2011/0174621 A1* | 7/2011 | Yonehara et al. | 204/451 |

FOREIGN PATENT DOCUMENTS

| | | |
|---|---|---|
| JP | 05-057114 A | 3/1993 |
| JP | H09-510792 A | 10/1997 |
| JP | 2006-145537 A | 6/2006 |
| JP | 2008-032676 A | 2/2008 |
| JP | 2009-109230 A | 5/2009 |
| WO | 00/63683 A1 | 10/2000 |
| WO | 2008/136321 A1 | 11/2008 |
| WO | 2009/062967 A1 | 5/2009 |
| WO | 2010/010859 A1 | 1/2010 |

OTHER PUBLICATIONS

Chinese Office Action issued in corresponding Chinese Patent Application No. 201410030477.4 dated Oct. 29, 2015.
Office Action issued in corresponding Japanese Patent Application No. 2014-003525 dated Feb. 3, 2015.
Extended European Search Report issued in corresponding European Patent Application No. 14152153A dated Apr. 29, 2014.
Chinese Office Action issued in corresponding Chinese Patent Application No. 201410030477.4 dated Jan. 16, 2017.

* cited by examiner

SAMPLE ANALYSIS METHOD AND SOLUTION TO BE USED THEREIN

CROSS-REFERENCE TO RELATED APPLICATIONS

The present application claims priority based on Japanese Patent Application No. 2013-9469 filed in Japan on Jan. 22, 2013 and Japanese Patent Application No. 2014-003525 filed in Japan on Jan. 10, 2014, both of which are incorporated herein by reference in their entireties.

BACKGROUND

1. Field of the Disclosure

The present disclosure relates to a sample analysis method, a solution for capillary electrophoresis, and a sample analysis kit.

2. Description of Related Art

As a method for analyzing blood protein through use of capillary electrophoresis, WO 2010-010859 discloses a method involving analyzing hemoglobin through use of capillary electrophoresis. WO 2010-010859 discloses a running buffer solution having a pH of 4.8 containing fumaric acid, sodium thiocyanate, arginine, and chondroitin sulfate C. WO 2010-010859 discloses that analysis time of blood protein is 35 seconds or less.

JP 2009-109230 A discloses that stable HbA1c is measured by capillary electrophoresis. JP 2009-109230 A discloses a citrate buffer solution (pH 6.0) containing sodium nitrite and a surfactant or a malate buffer solution (pH 5.2) containing potassium nitrite and dextran sulfate, as a running buffer solution.

JP 2006-145537 A discloses that hemoglobin is analyzed by capillary electrophoresis using a zwitterionic buffer containing a flow inhibitor such as aliphatic diamine or aliphatic polyamine. JP 2006-145537 A discloses a tricine/1,4-diaminobutane buffer (pH 9.37), a tricine/1,5-diaminopentane buffer (pH 9.37), a tricine/diethylenetriamine buffer (pH 9.40), a tricine/N,N,N',N'-tetramethyl-1,4-butadieneamine buffer (pH 9.19), as an analysis buffer solution.

JP 09 (1997)-510792 A discloses a buffer solution containing water, a saccharide-conjugated compound (boric acid, borax, etc.), a basic compound sufficient to adjust the buffer solution to pH 9 to 12, and a zwitterionic compound having a pKa of 9 to 12.

WO 2008-136321 discloses a method for analyzing hemoglobin by capillary electrophoresis. WO 2008-136321 discloses a buffer solution obtained by adding a non-ionic surfactant (dodecylmaltoside, etc.) to a buffer solution (pH 4.8) containing fumaric acid, argininic acid, and chondroitin sulfate C, as a buffer solution to be contained in a capillary tube.

SUMMARY

A sample analysis method using capillary electrophoresis has advantages in that the amount of a sample to be required is small and an apparatus can be miniaturized. On the other hand, further enhancement of accuracy and shortening of analysis time are expected from the viewpoint of a use in a clinical test.

However, when an attempt is made so as to shorten analysis time, there arise the following problems: an increase in current value and/or heat generation occur, and there are risks of thermal denaturation of hemoglobin, an increase in peak width, generation of methemoglobin, formation of air bubbles in a capillary, and the like, with the result that analysis accuracy becomes insufficient. For example, the method of WO 2010-010859 has a problem of thermal denaturation of hemoglobin, and the method of JP 2009-109230 A has a problem of an increase in heat generation amount caused by an increase in current value due to the addition of nitrite. In both of the cases, it is difficult to enhance analysis accuracy. Further, the methods of JP 2006-145537 A and JP 09 (1997)-510792 A have a problem in that measurement time becomes long (for example, 10 minutes or more), and hence the methods of those documents cannot be substantially applied to a clinical test in which it is desired to treat a great number of samples in a short period of time. Further, the method of WO 2008-136321 has a problem in that hemoglobin is denatured by the function of a surfactant, and there are risks of an increase in peak width, generation of methemoglobin, and the like, with the result that analysis becomes insufficient.

Therefore, with the foregoing in mind, in one aspect, the present disclosure provides a sample analysis method using capillary electrophoresis capable of enhancing analysis accuracy, a solution for capillary electrophoresis, and a sample analysis kit.

In one aspect, the present disclosure relates to a sample analysis method, including separating and/or detecting a substance to be analyzed in a sample by capillary electrophoresis, wherein the substance to be analyzed is separated and/or detected in the presence of a pH buffer substance and a non-surfactant-type zwitterionic substance.

In another aspect, the present disclosure relates to a solution for capillary electrophoresis, containing a pH buffer substance, a non-surfactant-type zwitterionic substance, and water.

In still another aspect, the present disclosure relates to a sample analysis kit, including: the solution for capillary electrophoresis of the present disclosure and a capillary electrophoresis chip, wherein the capillary electrophoresis chip includes a sample holding tank, a running buffer solution holding tank, and a capillary flow path, in which the sample holding tank and the running buffer solution holding tank communicate with each other through the capillary flow path.

According to the present disclosure, in one aspect, there can be provided a sample analysis method using capillary electrophoresis capable of enhancing analysis accuracy, a solution for capillary electrophoresis, and a sample analysis kit.

DETAILED DESCRIPTION

Figure 1:
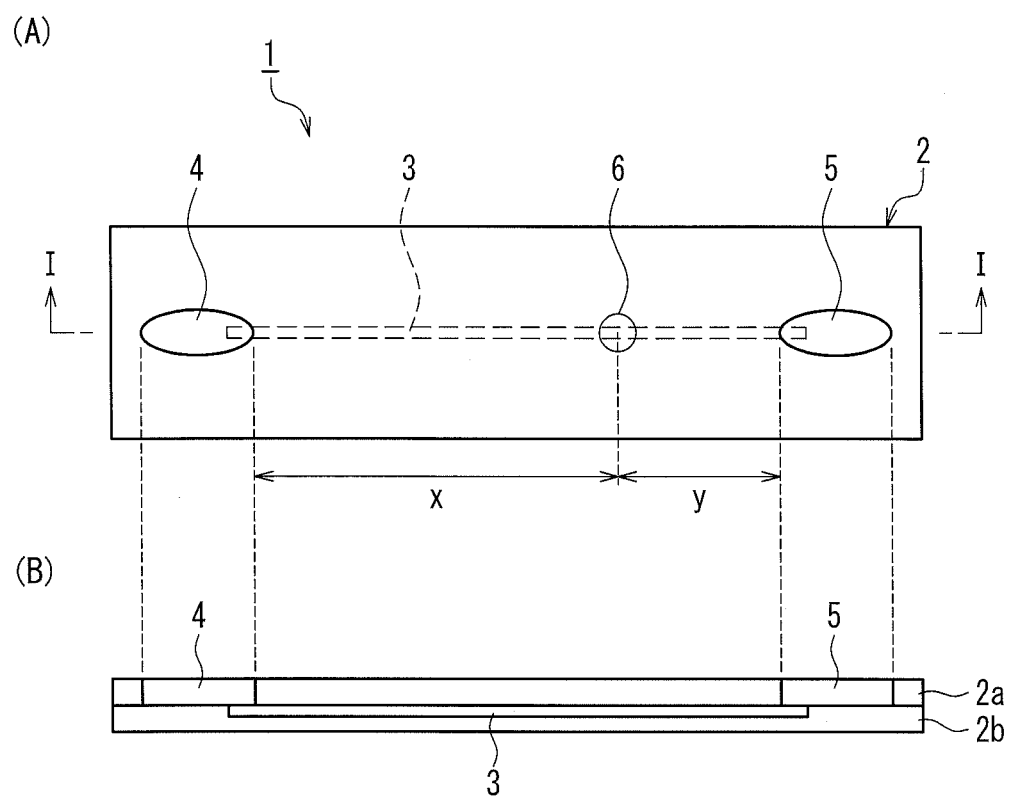
FIG. 1A is a plan view of a capillary electrophoresis chip according to an embodiment of the present disclosure.
FIG. 1B is a sectional view of the electrophoresis chip shown in FIG. 1A when viewed in an I-I direction.
Figure 2A:
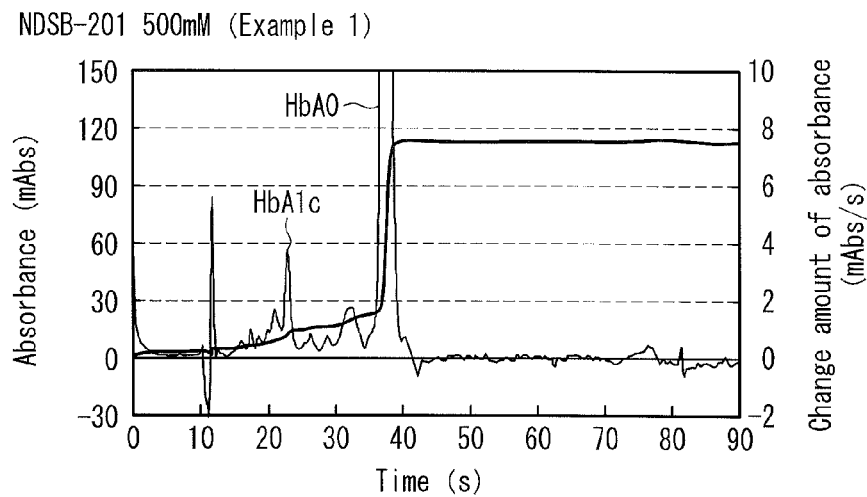
FIG. 2A shows an example of an electroferrogram obtained by capillary electrophoresis using a solution for capillary electrophoresis of Example 1.
Figure 2B:
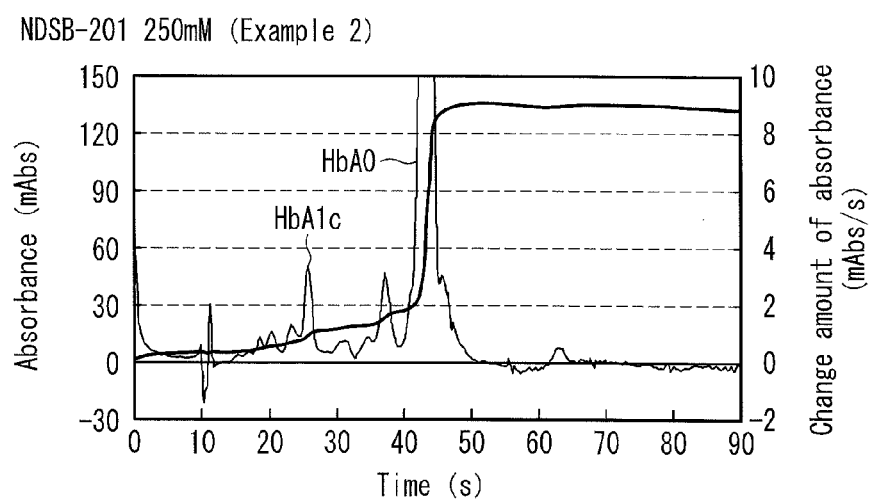
FIG. 2B shows an example of an electroferrogram obtained by capillary electrophoresis using a solution for capillary electrophoresis of Example 2.
Figure 2C:
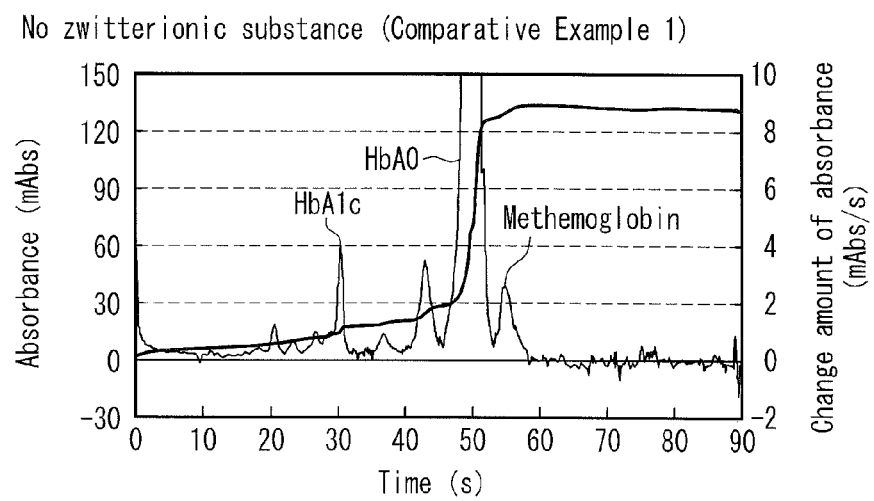
FIG. 2C shows an example of an electroferrogram obtained by capillary electrophoresis using a solution for capillary electrophoresis of Comparative Example 1.
Figure 3A:
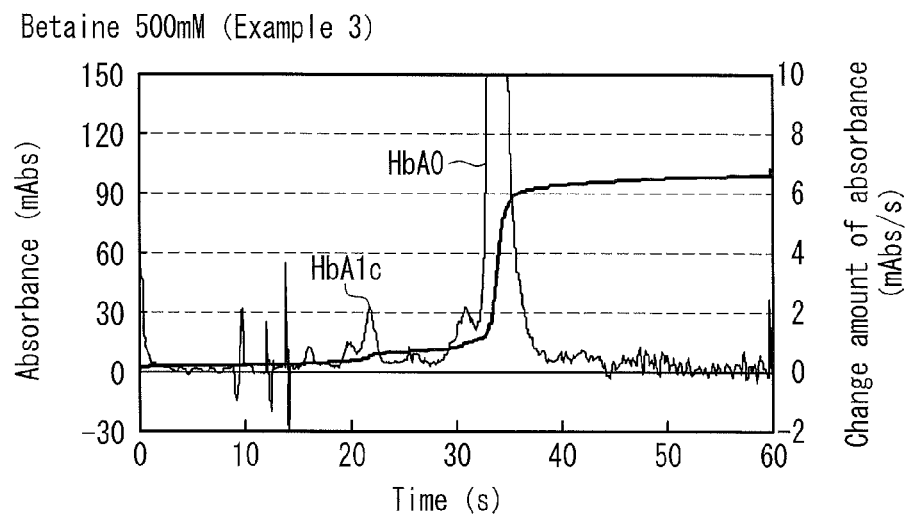
FIG. 3A shows an example of an electroferrogram obtained by capillary electrophoresis using a solution for capillary electrophoresis of Example 3.
Figure 3B:
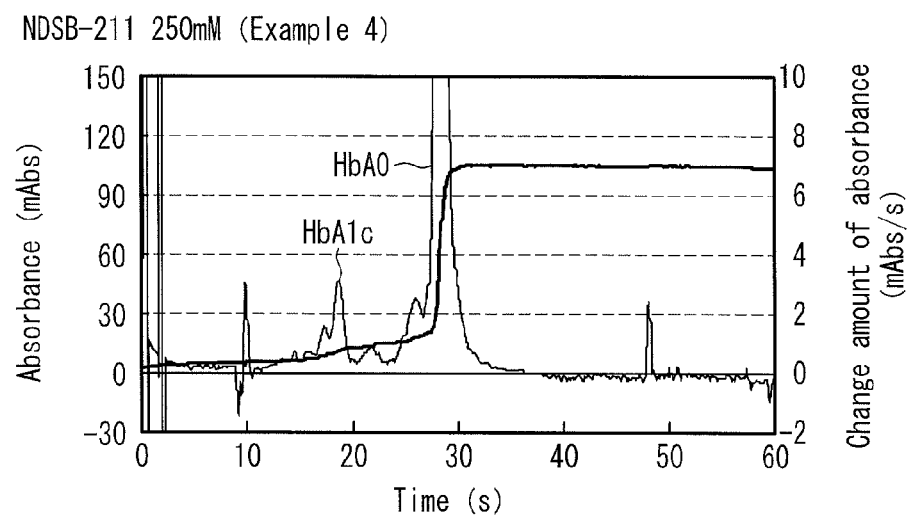
FIG. 3B shows an example of an electroferrogram obtained by capillary electrophoresis using a solution for capillary electrophoresis of Example 4.
Figure 3C:
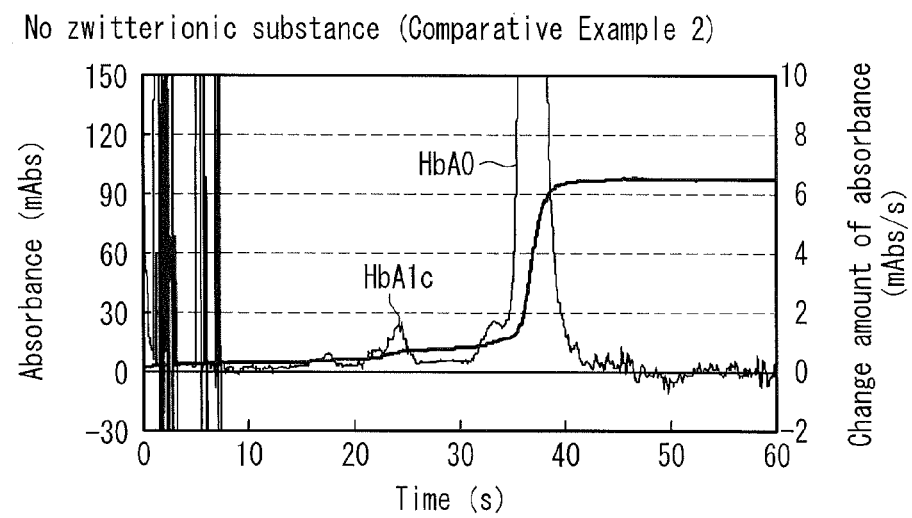
FIG. 3C shows an example of an electroferrogram obtained by capillary electrophoresis using a solution for capillary electrophoresis of Comparative Example 2.

In one aspect, the present disclosure is based on the following finding: when a substance group to be separated and a non-surfactant-type zwitterionic substance are allowed to be present during capillary electrophoresis, heat generation can be prevented by decreasing a current value during electrophoresis, and thus analysis accuracy can be enhanced. That is, in one aspect, the present disclosure relates to a sample analysis method including separating and/or detecting a substance to be analyzed in a sample by capillary electrophoresis, in which the substance to be analyzed is separated and/or detected in the presence of a pH buffer substance and a non-surfactant-type zwitterionic substance. Further, in another aspect, the present disclosure relates to a sample analysis method including: introducing a sample into a capillary flow path filled with a running buffer solution; and separating and/or detecting a substance to be analyzed in the sample through capillary electrophoresis by applying a voltage to a whole or a part of the capillary flow path, in which the substance to be analyzed is separated and/or detected in the presence of a pH buffer substance and a non-surfactant-type zwitterionic substance.

[Non-Surfactant-Type Zwitterionic Substance]

In one or a plurality of embodiments, the term "non-surfactant-type" as used herein refers to not forming a micelle. In one or a plurality of embodiments, the term "not forming a micelle" as used herein refers to not forming a micelle or not substantially forming a micelle in an aqueous medium. In one or a plurality of embodiments, the term "not forming a micelle or not substantially forming a micelle" as used herein refers to that a critical micelle concentration (CMC) is 200 mmol/L or more, 300 mmol/L or more, or the zwitterionic substance has no CMC, from the viewpoint of enhancing analysis accuracy.

Further, in one or a plurality of embodiments, the non-surfactant-type zwitterionic substance is a substance not having a pH buffering action, or a substance not exhibiting a pH buffering action or not substantially exhibiting a pH buffering action at a running condition pH, from the viewpoint of enhancing analysis accuracy. In one or a plurality of non-limiting embodiments, even when 100 mmol/L of the non-surfactant-type zwitterionic substance is added in the case where the concentration of a pH buffer substance (described later) having a pKa in the vicinity of the running condition pH is 40 mmol/L, the pH do not change or do not substantially change, or with the change being limited to 0.2 or less or 0.1 or less. In one or a plurality of embodiments, the term "running condition pH" as used herein refers to the pH of a running buffer solution with which a capillary is to be filled before running or the pH of a sample or a sample preparation solution for preparing a sample.

In the present disclosure, in one or a plurality of non-limiting embodiments, as the "zwitterionic substance", there are given zwitterions and betaine. In one or a plurality of embodiments, the term "zwitterions" as used herein refer to molecules having both positive charge and negative charge in one molecule, which are also called an inner salt. The term "betaine" as used herein refers to a compound which has positive charge and negative charge at positions not adjacent to each other in the same molecule, in which a dissociable hydrogen atom is not bonded to an atom having positive charge, and which has no charge as the entire molecules. In one or a plurality of embodiments, the term "betaine" as used herein includes sulfobetaine containing a sulfo group ($-SO_3^-$) as a group imparting negative charge, carboxybetaine containing a carboxyl group ($-COO^-$) as a group imparting negative charge, and phosphobetaine containing a phosphate group ($-PO_4^-$) as a group imparting negative charge.

In one or a plurality of embodiments, the non-surfactant-type zwitterionic substance is non-surfactant-type betaine, non-surfactant-type sulfobetaine and carboxybetaine, a non-surfactant-type substance having a quaternary ammonium cation and a sulfo group ($-SO_3^-$) or a carboxyl group ($-COO^-$) at positions not adjacent to each other in the same molecule, or a non-surfactant-type sulfobetaine (NDSB), from the viewpoint of enhancing analysis accuracy. In one or a plurality of non-limiting embodiments, as the NDSB, there is given a substance represented by any of the following formulae.

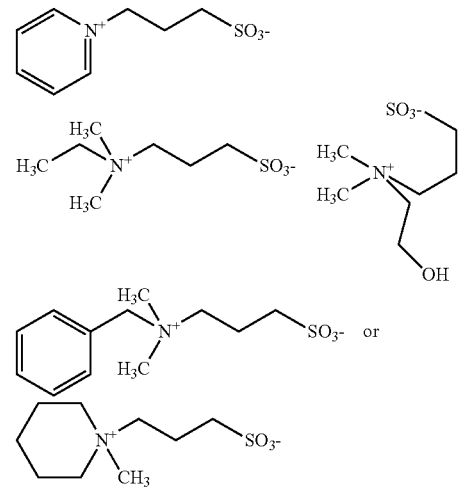

[pH Buffer Substance]

In one or a plurality of embodiments, the term "pH buffer substance" as used herein refers to a substance having a pKa or pKb in the vicinity of the running condition pH and an acid or a base to be a counter ion of the substance. In one or a plurality of non-limiting embodiments, the vicinity of the running condition pH is in a range of ±2.5, ±2.0, ±1.5, or ±1.0 of the running condition pH from the viewpoint of enhancing analysis accuracy.

Electrophoresis is a method for separating a substance to be analyzed depending on a charged state thereof, and hence it is preferred to define the charged state of a substance to be analyzed to be a predetermined state during analysis from the viewpoint of enhancing analysis accuracy. The charged state of a substance to be analyzed is influenced by the surrounding pH and a substance that is positively or negatively charged at the running condition pH. Therefore, it is preferred that the charged state of a substance to be analyzed be set to be a predetermined state by adding the "pH buffer substance", that is, a substance having a pKa or pKb in the vicinity of the running condition pH and an acid or a base to be a counter ion of the substance. Thus, in the present disclosure, the pH buffer substance is at least one compound and may be a combination of a plurality of kinds of compounds.

In one or a plurality of non-limiting embodiments, in the case where the running condition pH is 5.3, citric acid (pKa=4.8) or propionic acid (pKa=4.9) serving as an acid having a pKa in the vicinity of pH 5.3, etc. and sodium or arginine serving as a base to be a counter ion of citric acid or propionic acid, etc. are added. Alternatively, creatinine (pKa=4.83) serving as a base having a pKa in the vicinity of pH 5.3, etc. and chlorine serving as an acid to be a counter ion of creatinine, etc. are added. In one or a plurality of other non-limiting embodiments, in the case where the running condition pH is 7.2, phosphoric acid (pKa=7.2) serving as an acid having a pKa in the vicinity of pH 7.2, etc. and sodium or arginine serving as a base to be a counter ion of phosphoric acid, etc. are added. Alternatively, tris (pKa=8.0) serving as a base having a pKa in the vicinity of pH 7.2, etc. and chlorine serving as an acid to be a counter ion of tris, etc. are added.

In one or a plurality of non-limiting embodiments, examples of the pH buffer substance include: an organic acid, an inorganic acid, an amino acid; an acid or a base to be a counter ion thereof; and a combination thereof. In one or a plurality of non-limiting embodiments, examples of the organic acid include maleic acid, tartaric acid, succinic acid, fumaric acid, phthalic acid, malonic acid, malic acid, citric acid, MES (2-Morpholinoethanesulfonic acid, monohydrate), ADA (N-(2-Acetamido)iminodiacetic acid), ACES (N-(2-Acetamido)-2-aminoethanesulfonic acid), BES (N,N-Bis(2-hydroxyethyl)-2-aminoethanesulfonic acid), MOPS (3-Morpholinopropanesulfonic acid), TES (N-Tris(hydroxymethyl) methyl-2-aminoethanesulfonic acid), HEPES (2-[4-(2-Hydroxyethyl)-1-piperazinyl]ethanesulfonic acid), TRICINE (N-[Tris(hydroxymethyl) methyl]glycine), PIPES (piperazine-1,4-bis(2-ethanesulfonic acid)), POPSO (piperazine-1,4-bis(2-hydroxy-3-propanesulfonic acid), dehydrate), carboxylic acid, and a combination thereof. In one or a plurality of non-limiting embodiments, examples of the inorganic acid include phosphoric acid and boric acid. Examples of the amino acid include glycine, alanine, leucine, and a combination thereof. In one or a plurality of non-limiting embodiments, a base is used in addition to the organic acid, the inorganic acid, and/or the amino acid. In one or a plurality of non-limiting embodiments, examples of the base include a strong base, a weak base, and a diamine compound. In one or a plurality of non-limiting embodiments, examples of the strong base include sodium and potassium. In one or a plurality of non-limiting embodiments, examples of the weak base include arginine, lysine, histidine, trishydroxy methyl amino methane, dimethylaminoethanol, triethanolamine, diethanolamine, and creatinine. As the diamine compound, there is given 1,4-diaminobutane or the like.

When the weak base is used, a current value during electrophoresis can be suppressed because an ion movement speed is lower than that in the case of using the strong base. In a speed of an electroosmotic flow, the weak base having a lower ion movement speed seems to have a low speed of an electroosmotic flow. However, most of the weak bases have a large molecular weight compared with that of the strong base, and hence the speed of an electroosmotic flow remains the same or is not greatly lost. Thus, in one or a plurality of non-limiting embodiments, the pH buffer substance contains the weak base from the viewpoint of enhancing analysis accuracy.

[Ionic Pseudostationary Phase]

As capillary electrophoresis, there is given electrodynamic chromatography using a pseudostationary phase. For example, WO 2010-010859 discloses that blood protein is separated through use of an anionic group-containing compound such as chondroitin sulfate, that is, an ionic pseudostationary phase. In the capillary electrophoresis using an ionic pseudostationary phase, substances in a sample and an ionic pseudostationary phase are allowed to interact with each other during electrophoresis to separate the substances in accordance with affinity (difference in a distribution coefficient) with the ionic pseudostationary phase, whereby a substance is separated from another substance.

It has been proposed to add a betaine-type amphoteric surfactant to a running buffer solution in the capillary electrophoresis using an ionic pseudostationary phase (for example, WO 2010-010859). However, when a betaine-type amphoteric surfactant is added to a running buffer solution, although a current value declines, measurement time is extended or a peak width is increased.

In another aspect, the present disclosure is based on the finding that, when a non-surfactant-type zwitterionic substance is allowed to be present in a place where a substance group to be separated and an ionic pseudostationary phase interact with each other during capillary electrophoresis using an ionic pseudostationary phase, measurement time can be shortened while an increase in a current value is suppressed. Although the detail of the mechanism in which measurement time can be shortened while an increase in a current value is suppressed by a non-surfactant-type zwitterionic substance is not clear, the following is presumed. That is, the interaction between the substance group to be separated and the ionic pseudostationary phase is inhibited by the non-surfactant-type zwitterionic substance, with the result that the turnover of the interaction between the substance group to be separated and the ionic pseudostationary phase is accelerated. The foregoing is presumed to shorten the measurement time. It should be noted that the mechanism in the present disclosure is not limited to the foregoing.

Thus, in another aspect, the present disclosure relates to a sample analysis method involving separating and/or detecting a substance to be analyzed in a sample by capillary electrophoresis, in which the substance to be analyzed is separated and/or detected in the presence of an ionic pseudostationary phase, a pH buffer substance, and a non-surfactant-type zwitterionic substance. According to this aspect, a sample analysis method using capillary electrophoresis capable of enhancing analysis accuracy and shortening measurement time can be provided.

In one or a plurality of embodiments, the term "ionic pseudostationary phase" as used herein refers to an ionic substance used in capillary electrophoresis for the purpose of separating substances in a sample in accordance with affinity (difference in a distribution coefficient) to separate a substance from another substance. In one or a plurality of embodiments, as the ionic pseudostationary phase, an ionic pseudostationary phase that has already been used or that can be used in the future can be selected and used in accordance with a sample and/or a substance to be analyzed. In one or a plurality of embodiments, the ionic pseudostationary phase may be an anionic or cationic polymer. The above-mentioned polymer may be a polysaccharide from the viewpoint of enhancing analysis accuracy and shortening measurement time.

[Substance to be Analyzed]

In one or a plurality of non-limiting embodiments, examples of the term "substance to be analyzed" as used herein include protein, biological substance, and blood substance. Specific examples of the protein include hemoglobin, albumin, and globulin. In one or a plurality of non-limiting embodiments, examples of the hemoglobin include glycosylated hemoglobin, HbA1c, mutant hemoglobin, minor hemoglobin, and modified hemoglobin. More specific examples thereof include stable HbA1c (s-HbA1c), hemoglobin A0 (HbA0), hemoglobin A1a (HbA1a), hemoglobin A1b (HbA1b), hemoglobin A1d (HbA1d), hemoglobin A1e (HbA1e), hemoglobin A2 (HbA2), hemoglobin S (HbS, sickle-cell hemoglobin), hemoglobin F (HbF, fetal hemoglobin), hemoglobin M (HbM), hemoglobin C (HbC), hemoglobin D (HbD), hemoglobin E (HbE), methemoglobin, carbamylated hemoglobin, acetylated hemoglobin, aldehyde hemoglobin, and labile HbA1c (l-HbA1c). In one or a plurality of non-limiting embodiments, examples of the biological substance and the blood substance include bilirubin, hormone, and metabolite. Examples of the hormone include thyroid-stimulating hormone, adrenocorticotropic hormone, human chorionic gonadotropin, insulin, glucagons, adrenal cortical hormone, epinephrine, norepinephrine, androgen, estrogen, progesteron, aldosterone, and cortisol. In one or a plurality of non-limiting embodiments, examples of the substance to be analyzed in the case of using the above-mentioned ionic pseudostationary phase include glycosylated hemoglobin, mutant hemoglobin, minor hemoglobin, modified hemoglobin, and a combination thereof.

In one or a plurality of non-limiting embodiments, the term "sample" as used herein refers to a sample prepared from a sample raw material or a sample raw material itself. In one or a plurality of non-limiting embodiments, examples of the sample raw material include a material containing the above-mentioned substance to be analyzed and/or a biological sample. In one or a plurality of non-limiting embodiments, examples of the biological sample include blood, a substance derived from blood containing a red blood cell component, saliva, and spinal fluid. As the blood, there is given blood collected from a living body, and in one or a plurality of non-limiting embodiments, examples of the blood include blood of an animal, blood of a mammal, and blood of a human. As the substance derived from blood containing a red blood cell component, there is given a red blood cell component that is separated or prepared from blood, and in one or a plurality of non-limiting embodiments, examples of the substance derived from blood include a blood cell fraction from which blood plasma has been removed, a blood cell concentrate, freeze-dried blood or blood cells, a hemolyzed sample prepared by hemolyzing whole blood, centrifuged blood, spontaneously-sedimented blood, and washed blood cells.

In sample analysis using capillary electrophoresis, a calibration material is sometimes used for the purpose of enhancing the accuracy and reproducibility of analysis. Further, a control material is sometimes used for the purpose of managing or maintaining the accuracy and reproducibility of analysis. Therefore, in one or a plurality of non-limiting embodiments, the term "sample" or "sample raw material" as used herein can include a calibration material and a control material. It should be noted that the term "calibration material" as used herein includes, for example, a standard material to be used for calibration of an apparatus. The term "control material" includes a sample to be used for managing or maintaining the accuracy and/or reproducibility of analysis, and examples thereof include control serum, pooled serum, control whole blood, and a standard liquid.

In one or a plurality of non-limiting embodiments, in the case where a substance to be analyzed has positive charge as in hemoglobin or HbA1c, the ionic pseudostationary phase is a polysaccharide having an anionic group from the viewpoint of enhancing analysis accuracy and shortening measurement time. Examples of the polysaccharide having an anionic group include sulfated polysaccharides, carboxylated polysaccharides, sulfonated polysaccharides, and phosphorylated polysaccharides. In one or a plurality of non-limiting embodiments, the polysaccharide having an anionic group includes the sulfated polysaccharides and the carboxylated polysaccharides from the viewpoint of enhancing analysis accuracy and shortening measurement time. In one or a plurality of non-limiting embodiments, examples of the sulfated polysaccharides include chondroitin sulfate, heparin, heparan, fucoidan, and salts thereof. In one or a plurality of non-limiting embodiments, the sulfated polysaccharides include chondroitin sulfate or salts thereof. Examples of the chondroitin sulfate include chondroitin sulfate A, chondroitin sulfate C, chondroitin sulfate C, and chondroitin sulfate E. Examples of the carboxylated polysaccharides include alginic acid, hyaluronic acid, and salts thereof. In the case where the polysaccharide having an anionic group is a salt, examples of a counter ion thereof include ions of an alkali metal, an alkaline earth metal, an amine compound, and an organic base. Examples of the carboxylated polysaccharides include a sodium salt, a potassium salt, a lithium salt, a calcium salt, an ammonium salt, a tris salt, an arginine salt, a lysine salt, a histidine salt, a trishydroxy methyl amino methane salt, a dimethylaminoethanol salt, a triethanolamine salt, a diethanolamine salt, and a creatinine salt. In one or a plurality of non-limiting embodiments, the carboxylated polysaccharides include alginic acid or salts thereof (for example, sodium alginate) from the viewpoint of enhancing analysis accuracy and shortening measurement time. Further, in one or a plurality of embodiments in which a substance to be analyzed is hemoglobin or HbA1c, the separation and/or detection of a substance to be analyzed by capillary electrophoresis is performed through use of a solution for capillary electrophoresis and/or a running buffer solution having a pH of 3.0 to 6.9 or 4.0 to 6.0 from the viewpoint of enhancing analysis accuracy.

[Solution for Capillary Electrophoresis]

In one or a plurality of non-limiting embodiments, the term "solution for capillary electrophoresis" as used herein refers to a solution that can be used as at least one of a running buffer solution with which a capillary flow path is to be filled before capillary electrophoresis, a running buffer solution to be used in place of a sample after the sample has been introduced into a capillary, a solution for preparing these running buffer solutions, and a solution for preparing a sample (hereinafter, which may be also referred to as "sample preparation solution". The running buffer solution with which a capillary flow path is to be filled before capillary electrophoresis and the running buffer solution to be used in place of a sample after the sample has been introduced into a capillary may have the same solution composition or different solution compositions.

In one aspect, the present disclosure relates to a solution for capillary electrophoresis containing a pH buffer substance, a non-surfactant-type zwitterionic substance, and water. In one or a plurality of embodiments, the solution for capillary elecrophoresis of the present disclosure can be used for the sample analysis method of the present disclosure, which can contribute to the enhancement of the analysis accuracy of sample analysis.

In another aspect, the present disclosure relates to a solution for capillary electrophoresis containing an ionic pseudostationary phase, a pH buffer substance, a non-surfactant-type zwitterionic substance, and water. In one or a plurality of embodiments, the solution for capillary electrophoresis of the present disclosure can be used for the sample analysis method of the present disclosure, which can contribute to the enhancement of analysis accuracy of sample analysis and the shortening of measurement time.

In the sample analysis method of the present disclosure, the solution for capillary electrophoresis of the present disclosure is used at least as a sample preparation solution from the viewpoint of enhancing analysis accuracy. In one or a plurality of non-limiting embodiments of the sample analysis method of the present disclosure, the solution for capillary electrophoresis of the present disclosure can be used in the following cases:

Case in which the solution for capillary electrophoresis is used only as a sample preparation solution;

Case in which the solution for capillary electrophoresis is used as a running buffer solution or a solution for preparing the running buffer solution, and a sample preparation solution;

Case in which the solution for capillary electrophoresis is used as a running buffer solution to be used in place of a sample after the sample has been introduced into a capillary or a solution for preparing the running buffer solution, and a sample preparation solution;

Case in which the solution for capillary electrophoresis is used only as a running buffer solution or a solution for preparing the running buffer solution;

Case in which the solution for capillary electrophoresis is used only as a running buffer solution to be used in place of a sample after the sample has been introduced into a capillary or a solution for preparing the running buffer solution; and Case in which the solution for capillary electrophoresis is used as a running buffer solution or a solution for preparing the running buffer solution, a running buffer solution to be used in place of a sample after the sample has been introduced into a capillary or a solution for preparing the running buffer solution, and a sample preparation solution.

Those skilled in the art can appropriately determine in which embodiment the solution for capillary electrophoresis of the present disclosure is used so as to perform the sample analysis method of the present disclosure, in accordance with a substance to be analyzed, a pH buffer substance, a non-surfactant-type zwitterionic substance, and an ionic pseudostationary phase (if it is used).

[Non-Surfactant-Type Zwitterionic Substance]

The description and embodiments of the non-surfactant-type zwitterionic substance are as shown above. In the case where the solution for capillary electrophoresis of the present disclosure is used as a running buffer solution, in one or a plurality of embodiments, the content of the non-surfactant-type zwitterionic substance in the solution for capillary electrophoresis of the present disclosure is 10 to 2,000 mM, 100 to 1,000 mM, or 200 to 600 mM from the viewpoint of enhancing analysis accuracy.

[pH Buffer Substance]

The description and embodiments of the pH buffer substance are as shown above. In the case where the solution for capillary electrophoresis of the present disclosure is used as a running buffer solution, in one or a plurality of embodiments, the content of the pH buffer substance in the solution for capillary electrophoresis of the present disclosure is 5 to 500 mM, 10 to 300 mM, or 20 to 100 mM from the viewpoint of enhancing analysis accuracy.

[Ionic Pseudostationary Phase]

The description and embodiments of the ionic pseudostationary phase are as shown above. In the case where the solution for capillary electrophoresis of the present disclosure is used as a running buffer solution, and the ionic pseudostationary phase is used for the purpose of shortening measurement time, in one or a plurality of embodiments, the content of the ionic pseudostationary phase in the solution for capillary electrophoresis of the present disclosure is 0.001 to 10 w/v %, or 0.1 to 5 w/v % from the viewpoint of enhancing analysis accuracy and shortening measurement time.

[Water]

The solution for capillary electrophoresis of the present disclosure contains water as a medium. In one or a plurality of embodiments, in the case where the solution for capillary electrophoresis of the present disclosure contains a buffer solution, the term "water as a medium" as used herein includes water contained in the buffer solution. As the water, distilled water, ion exchange water, pure water, ultrapure water, or the like can be used.

[Preservative]

The solution for capillary electrophoresis of the present disclosure may contain a preservative for suppressing the propagation of microorganisms, and may contain, for example, sodium azide, ethylparaben, proclin, and the like.

[pH of Solution for Capillary Electrophoresis]

The pH of the solution for capillary electrophoresis of the present disclosure can be selected and used from a pH range that has already been used or can be used in the future, in accordance with a sample and/or a substance to be analyzed. In one or a plurality of embodiments, the pH can be adjusted by adding an acid or a base as necessary. In one or a plurality of embodiments, in the case where a substance to be analyzed is hemoglobin, the pH of the solution for capillary electrophoresis is 3.0 to 6.9 or 4.0 to 6.0 from the viewpoint of enhancing analysis accuracy. It should be noted that the above-mentioned pH refers to a pH of the solution for capillary electrophoresis at 25° C., which is a numerical value measured through use of a pH meter and obtained after an electrode has been immersed in the solution for 40 minutes.

[Other Components]

In one or a plurality of embodiments, the solution for capillary electrophoresis of the present disclosure may contain a non-ionic surfactant from the viewpoint of treating a sample raw material as a sample preparation solution (for example, accelerating the hemolyzation of blood cells). In one or a plurality of embodiments, the concentration of a non-ionic surfactant in the solution for capillary electrophoresis of the present disclosure is 0.01 w/v % or more, or 0.05 w/v % or more from the viewpoint of solubilizing an insoluble component. Further, the concentration of the non-ionic surfactant is 2 w/v % or less, or 1 w/v % or less from the viewpoint of facilitating handling.

[Organic Acid, Base]

Further, in one or a plurality of embodiments, the solution for capillary electrophoresis of the present disclosure can further contain an organic acid or a base. In the case of using an anionic pseudostationary phase or a cationic pseudostationary phase in the solution for capillary electrophoresis through use of a capillary whose capillary inner wall is covered with a cationic substance or an anionic substance, respectively, the anionic pseudostationary phase or the cationic pseudostationary phase may be electrically connected to the capillary inner wall to cover the capillary inner wall. In this case, when the molecular weight of the pseudostationary phase is large, the pseudostationary phase cannot completely cover the capillary inner wall, and the cationic substance or the anionic substance of the capillary inner wall may be exposed to the surface in a gap of the pseudostationary phase. In this case, when the solution for capillary electrophoresis or another solution that is to pass through the capillary contains an organic acid having two or more acid functional groups such as a carboxyl group and a sulfonic group or a base having two or more basic functional groups such as an amino group, one acid functional group of the organic acid is bonded to the cationic substance of the capillary inner wall or one basic functional group of the base is bonded to the anionic substance. Then, the remaining acid functional group of the organic acid or the remaining basic functional group of the base are exposed to the capillary inner wall, whereby the capillary inner wall can be rendered anionic or cationic effectively. As the above-mentioned organic acid, there are given maleic acid, tartaric acid, succinic acid, fumaric acid, phthalic acid, malonic acid, malic acid, citric acid, ADA, PIPES, and POPSO. As the above-mentioned base, there are given arginine and lysine. Thus, the solution for capillary electrophoresis of the present disclosure may contain these organic acids. These organic acids may be the same substance as the pH buffer substance.

Further, in one or a plurality of embodiments, in the case of rendering a capillary inner wall anionic through use of a capillary whose capillary inner wall is covered with a cationic substance, a compound having one basic functional group serving as a base and a functional group that is likely to be anionic such as a hydroxyl group is selected. Examples of the compound include trishydroxymethylaminomethane, dimethylaminoethanol, triethanolamine, and diethanolamine. In one or a plurality of embodiments, in the case of rendering a capillary inner wall cationic through use of a capillary whose capillary inner wall is covered with an anionic substance, a compound having one acid functional group serving as an acid and a functional group that is likely to be cationic such as primary to tertiary amino groups is selected. Examples of the compound include ACES, 4-aminobenzoic acid, and 3-aminobenzoic acid. When a divalent or higher acid and a divalent or higher base are used, the viscosity of a solution rises, with the result that the speed of an electroosmotic flow may decrease and analysis time may be delayed due to a decrease in ion speed. However, by using a combination of the above-mentioned base and acid, for example, a compound having one basic functional group serving as a base and a functional group that is likely to be anionic such as a hydroxyl group, analysis can be performed while keeping the speed of an electroosmotic flow and analysis time without changing the viscosity of a solution.

Thus, in one aspect, the present disclosure relates to a sample analysis method including: introducing a sample into a capillary flow path filled with a running buffer solution; and separating and/or detecting a substance to be analyzed in the sample through capillary electrophoresis by applying a voltage to a whole or a part of the flow path, the method further including bringing a solution containing an anionic pseudostationary phase and an acid having two or more acid functional groups or a solution containing a weakly basic compound having one basic functional group and a functional group that is likely to be anionic into contact with a capillary whose capillary inner wall is covered with a cationic substance.

[Method for Preparing Solution for Capillary Electrophoresis]

In one or a plurality of embodiments, the solution for capillary electrophoreses of the present disclosure can be prepared by mixing a pH buffer substance, a non-surfactant-type zwitterionic substance, water, and further an ionic pseudostationary phase as necessary so that final contents fall within the above-mentioned respective ranges. As another embodiment, a solution for capillary electrophoresis may be prepared as a concentrate.

[Sample Analysis Method]

In one or a plurality of embodiments, the term "separating and/or detecting a substance to be analyzed in a sample through capillary electrophoresis" in the sample analysis method of the present disclosure includes introducing a sample into a capillary flow path filled with a running buffer solution, and separating and/or detecting a substance to be analyzed in the sample through capillary electrophoresis by applying a voltage to a whole or a part of the capillary flow path.

The term "separating and/or detecting a substance to be analyzed" in the sample analysis method of the present disclosure may include the step of detecting a substance to be analyzed separated through capillary electrophoresis by an optical procedure. As the detection by an optical procedure, for example, there is given measurement of an absorbance. The wavelength of an absorbance can be appropriately determined in accordance with the kinds of a sample and a substance to be analyzed.

The sample analysis method of the present disclosure may further include the step of analyzing an electroferrogram obtained by an optical procedure. In the case of separating a substance to be analyzed in a sample while sampling it continuously (capillary electrophoresis), it is difficult to analyze the substance to be analyzed in the sample individually from an electroferrogram to be obtained. However, the substance to be analyzed in the sample can be separated and analyzed individually by performing analytic processing with respect to an electroferrogram. The analytic processing may include obtaining an electroferrogram separated in accordance with mobility (separation time) by subjecting an electroferrogram to an arithmetic operation, and may include determining a component ratio of the substance to be analyzed in the sample based on the height of each peak and/or the area of each peak in the electroferrogram after the arithmetic operation. Examples of the arithmetic operation include a differential process and a difference process.

In one or a plurality of embodiments, the capillary flow path in the sample analysis method of the present disclosure is a tube having an inner diameter of 100 μm or less. The cross-sectional shape of the tube is not particularly limited and may be a circle, a rectangle, or other shapes. Further, the length of a capillary is not particularly limited and is, for example, 10 to 150 mm or 20 to 60 mm in the sample analysis method of the present disclosure.

In one or a plurality of embodiments, the capillary electrophoresis in the sample analysis method of the present disclosure is conducted through use of a capillary electrophoresis chip in which a capillary flow path is formed into a microchip structure. In one or a plurality of embodiments, the capillary electrophoresis chip has a length of 10 to 200 mm, a width of 1 to 60 mm, and a thickness of 0.3 to 5 mm, or a length of 30 to 70 mm, a width of 1 to 60 mm, and a thickness of 0.3 to 5 mm. A non-limiting embodiment of the capillary electrophoresis chip is described later.

In the sample analysis method of the present disclosure, a running buffer solution and/or a detergent may be introduced into a flow path in place of a sample after the sample has been supplied to the flow path in an amount sufficient for analysis. In this case, the running buffer solution may be the same as or different from the running buffer solution with which the flow path has already been filled.

[Measurement Method of Substance to be Analyzed]

As still another aspect, the present disclosure relates to a measurement method of a substance to be analyzed in a sample including measuring a substance to be analyzed in a sample through use of the sample analysis method of the present disclosure. The sample and the substance to be analyzed are as shown above. In one non-limiting embodiment, the substance to be analyzed is hemoglobin, HbA1c, or stable HbA1c to be an index for diagnosing diabetes. Further, in one or a plurality of non-limiting embodiments, the measurement method of the present disclosure involves measuring stable HbA1c to be an index for diagnosing diabetes and other hemoglobin components. Thus, as still another aspect, the present disclosure relates to a measurement method of HbA1c including measuring HbA1c through use of the sample analysis method of the present disclosure. In one or a plurality of embodiments, the measurement method includes separating the stable HbA1c from the other hemoglobin components and measuring the stable HbA1c through use of the sample analysis method of the present disclosure from the viewpoint of diagnosing diabetes.

[Sample Analysis Kit]

As still another aspect, the present disclosure relates to a sample analysis kit containing the solution for capillary electrophoresis of the present disclosure and a capillary electrophoresis chip. In one or a plurality of non-limiting embodiments, as a capillary electrophoresis chip in the sample analysis kit of the present disclosure, there is given an electrophoresis chip which includes a sample holding tank, a running buffer solution holding tank, and a capillary flow path and in which the sample holding tank and the running buffer solution holding tank communicate with each other through the capillary flow path. In one or a plurality of non-limiting embodiments, the sample analysis kit of the present disclosure may further contain a calibration material and a control material.

Hereinafter, one non-limiting embodiment of the sample analysis method of the present disclosure is described.

Embodiment 1

The sample analysis method is described by way of an example using a capillary electrophoresis chip shown in FIG. 1, in which a sample raw material is whole blood and a substance to be analyzed is hemoglobin.

FIG. 1 is a conceptual diagram showing a configuration of a capillary electrophoresis chip according to one or a plurality of non-limiting embodiments, which is to be used in the sample analysis method of the present disclosure. A capillary electrophoresis chip 1 shown in FIG. 1 is configured in such a manner that an upper substrate 2a is stacked on a lower substrate 2b. The upper substrate 2a is provided with two through-holes, and the two through-holes are sealed with the lower substrate 2b to form a sample holding tank 4 and a running buffer solution holding tank 5. The lower substrate 2b is provided with an I-shaped groove, and the upper substrate 2a is stacked on an upper part of the groove to form a capillary flow path 3. The sample holding tank 4 and the running buffer solution holding tank 5 communicate with each other through the capillary flow path 3. A detection section 6 is disposed at a position of x mm from the sample holding tank 4 and y mm from the running buffer solution holding tank 5. The length (x+y) of the capillary flow path 3 is appropriately determined in accordance with the length of the capillary electrophoresis chip, and is 10 to 150 mm or 20 to 60 mm in one or a plurality of non-limiting embodiments. In one or a plurality of non-limiting embodiments, the inner diameter of the capillary flow path 3 is 100 µm or less, 10 to 100 µm, or 25 to 75 µm. Further, there is no particular limit to the shape of the capillary flow path 3, and the flow path 3 may have a rectangular or other shapes. In one or plurality of non-limiting embodiments, the capillary electrophoresis chip has a length of 10 to 200 mm, a width of 1 to 60 mm, and a thickness of 0.3 to 5 mm, or a length of 30 to 70 mm, a width of 1 to 60 mm, and a thickness of 0.3 to 5 mm.

Examples of the material for the capillary flow path 3 include glass, fused silica, plastic, and the like. Examples of the plastic material include polymethyl methacrylate (PMMA), polycarbonate, polystyrene, polyterafluoroethylene (PTFE), and polyether ether ketone (PEEK). In one or a plurality of non-limiting embodiments, the inner wall of the capillary flow path 3 may be covered with an anionic group-containing compound, a cationic group-containing compound, a nonpolar compound, or the like. For example, the inner wall of the capillary flow path 3 may be covered with a sililating agent, an anionic group-containing polysaccharide, a functional group-containing compound, or the like. The inner wall of the capillary flow path 3 can be covered with a sililating agent or the like by the same method as those described in, for example, International Publication No. 2008/029685, International Publication No. 2008/13465, JP 2009-186445 A, and JP 2011-239365. Further, the inner wall of the capillary flow path 3 may be covered with a substance such as a pseudostationary phase contained in a solution for capillary electrophoresis or another solution by causing the solution for capillary electrophoresis or another solution to pass through the inner wall. Further, the capillary flow path 3 may be a commercially available capillary.

The volumes of the sample holding tank 4 and the running buffer solution holding tank 5 are appropriately determined in accordance with the inner diameter, length, and the like of the capillary flow path 3. The volumes of the sample holding tank 4 and the running buffer solution holding tank 5 are respectively, for example, in a range of 1 to 1,000 mm³, or 5 to 100 mm³. The sample holding tank 4 and the running buffer solution holding tank 5 may be respectively provided with electrodes for applying a voltage to both ends of the capillary flow path 3.

In one or a plurality of embodiments, each upper surface of the capillary flow path 3, the sample holding tank 4, and the running buffer solution holding tank 5 be covered with a sealant or the like as necessary from the viewpoint of suppressing the evaporation of a sample and a running buffer solution and reducing a change in concentration.

Next, an example of a sample analysis method using the capillary electrophoresis chip shown in FIG. 1 is described.

First, the running buffer solution holding tank 5 of the capillary electrophoresis chip is filled with the solution for capillary electrophoresis of the present disclosure as a running buffer solution, and the capillary flow path 3 is filled with the running buffer solution through a capillary phenomenon.

Next, a sample is placed in the sample holding tank 4 of the capillary electrophoresis chip in which the capillary flow path 3 is filled with the solution for capillary electrophoresis of the present disclosure.

The sample to be placed in the sample holding tank 4 can be prepared by diluting whole blood serving as a sample raw material with the solution for capillary electrophoresis of the present disclosure. The dilution ratio of the sample raw material is for example 1.2 to 100 times, 2 to 30 times, or 3 to 15 times. Further, in the case where the sample raw material contains ion components to such a degree as to influence resolution, the dilution ratio of the sample raw material is for example 2 to 1,000 times, 5 to 300 times, or 10 to 200 times.

Then, a voltage is applied to both ends of the capillary flow path 3, that is, between the sample holding tank 4 and the running buffer solution holding tank 5. Consequently, the sample is introduced from the sample holding tank 4 to the capillary flow path 3 and separated in the capillary flow path 3, and the sample containing hemoglobin moves from the sample holding tank 4 to the running buffer solution holding tank 5. In one or a plurality of non-limiting embodiments, the voltage to be applied to both ends of the capillary flow path 3 is 0.5 to 10 kV, or 0.5 to 5 kV.

Then, measurement is conducted at a predetermined position. The measurement can be conducted by, for example, an optical procedure such as spectrophotometry. In the case where a substance to be analyzed is hemoglobin, in one or a plurality of embodiments, an absorbance is measured at a wavelength of 415 nm.

The position for conducting measurement, that is, the length required for separation (x in FIG. 1) can be appropriately determined in accordance with the length of the capillary flow path 3 or the like. For example, in the case where the length of the capillary flow path 3 is 10 to 150 mm, the position for conducting measurement is at 5 to 140 mm, 10 to 100 mm, or 15 to 50 mm from the end of the capillary flow path 3 on the sample holding tank 4 side.

By performing analysis as described above, hemoglobin can be measured. In one or a plurality of non-limiting embodiments, HbA1c and other hemoglobin components can be measured separately, or, stable HbA1c to be an index for diagnosing diabetes and other hemoglobin components can be measured separately. Examples of the other hemoglobin components include labile HbA1c, HbS, HbF, HbA2, and HbC. Further, by analyzing an obtained electroferrogram, for example, the ratio (% HbA1c) of HbA1c and the amount of HbA1c can be measured. Therefore, the sample analysis method of the present disclosure can be used for preventing, diagnosing, and treating diabetes, etc.

It should be noted that, in the above-mentioned embodiments, an example is described in which a hemolyzed sample obtained by hemolyzing whole blood is used as a sample raw material and a sample obtained by diluting the hemolyzed sample with a sample preparation solution is used as a sample to be analyzed, but the present disclosure is not limited thereto. The sample to be analyzed may be, for example, a sample raw material (for example, hemolyzed blood) collected from a living body or a sample obtained by diluting a sample raw material with a solvent (solution for capillary electrophoresis of the present disclosure). The sample raw material may be, for example, a blood sample containing blood or a sample containing a commercially available product containing hemoglobin. There is no particular limit to the blood sample, and for example, there is given a hemolyzed sample obtained by hemolyzing a blood cell-containing substance such as whole blood. There is no particular limit to the hemolyzation, and examples thereof include ultrasonic treatment, freezing and thawing treatment, pressure treatment, osmotic pressure treatment, and surfactant treatment. There is no particular limit to the osmotic pressure treatment, and a blood cell-containing substance such as whole blood may be treated with a hypotonic solution or the like. There is no particular limit to the hypotonic solution, and examples thereof include water and a buffer solution. The buffer solution is not particularly limited and may contain, for example, the above-mentioned buffer solution and additive. There is no particular limit to the surfactant treatment, and for example, there is given treatment using a non-ionic surfactant. There is no particular limit to the non-ionic surfactant, and for example, there is given polyoxyethyleneisooctylphenylether (trade name "Triton (registered trademark) X-100").

In one or a plurality of non-limiting embodiments, in the analysis of hemoglobin by the sample analysis method of the present disclosure, the solution for capillary electrophoresis of the present disclosure may contain anionic chaotropic ions. For example, the analysis of hemoglobin can be performed in the same way as in JP 2009-186445 A.

Further, in one or a plurality of non-limiting embodiments, in the analysis of hemoglobin by the sample analysis method of the present disclosure, the solution for capillary electrophoresis of the present disclosure may contain an acid substance having two or more carboxyl groups in which an acid dissociation constant (pKa) of at least two carboxyl groups is lower than the pH of a running buffer solution by more than 2.5, 2.0, 1.5 or 1.0. For example, the analysis of hemoglobin can be performed in the same way as in JP 2011-149934 A. In one or a plurality of non-limiting embodiments, examples of the acid substance include trans-1,2-cyclohexanediamine-N,N,N',N'-tetraacetic acid (CyDTA), 1,1-cyclohexane diacetic acid, ($1\alpha,2\alpha,4\alpha$)-1,2,4-cyclohexanetricarboxylic acid, 1,2,3,4,5,6-cyclohexanehexacarboxylic acid, L-glutamic acid, D-tartaric acid, L-tartaric acid, fumaric acid, citric acid, aspartic acid, phthalic acid, and D-malic acid.

Further, in one or a plurality of non-limiting embodiments, in the analysis of hemoglobin by the sample analysis method of the present disclosure, the solution for capillary electrophoresis of the present disclosure may have an alkyl group as a hydrophobic part and may contain a nonionic surfactant having a saccharide as a hydrophilic part. The sample may contain a betaine-type amphoteric surfactant, and for example, the analysis of hemoglobin can be performed in the same way as described in WO 2008-136321.

Further, in one or a plurality of non-limiting embodiments, in the analysis of hemoglobin by the sample analysis method of the present disclosure, the solution for capillary electrophoresis of the present disclosure may contain a hemoglobin modifying agent for uniforming the properties of hemoglobin and may contain, for example, sodium azide, and potassium ferricyanide.

[Calculation Method of Measurement Value]

In the case of measuring a substance to be analyzed in a sample by the above-mentioned sample analysis method, a relative concentration of a substance to be analyzed is sometimes calculated as a measurement value. For example, the ratio of stable HbA1c with respect to HbA (adult Hb) is sometimes calculated as a measurement value in a unit of HbA1c % (=stable HbA1c amount/Hba amount×100) and HbA1c mmol/mol (=stable HbA1c amount/HbA amount×

100). However, a great amount of mutant hemoglobin and minor hemoglobin that are hemoglobin components other than HbA is sometimes contained in a sample. Examples of the mutant hemoglobin include HBS, HbE, HbD, and HbM, and examples of the minor hemoglobin include HbF and HbA2. These mutant hemoglobin and minor hemoglobin are also glycosylated similarly to HbA to generate glycosylated mutant hemoglobin and glycosylated minor hemoglobin.

There are methods for measuring the ratio of stable HbA1c through use of an enzyme and an antibody, and according to the methods, in general, the ratio of stable HbA1c is determined as a measurement value by measuring the concentration of stable HbA1c and the concentration of hemoglobin. When a sample containing a great amount of mutant hemoglobin and minor hemoglobin is measured by these methods, there are the cases where the concentration of only stable HbA1c can be measured based on the specificity of an enzyme and an antibody and where the concentrations of glycosylated mutant hemoglobin and glycosylated minor hemoglobin as well as the concentration of stable HbA1c are measured. When the concentration of hemoglobin is measured, the concentration of total hemoglobin is measured without distinguishing mutant hemoglobin and minor hemoglobin from HbA in most cases. Therefore, in the case of measuring the concentrations of glycosylated mutant hemoglobin and glycosylated minor hemoglobin as well as the concentration of stable HbA1c, the value of a ratio of stable HbA1c is not influenced by mutant hemoglobin or minor hemoglobin, or the value of a ratio is relatively weakly influenced even when influenced. However, in the case of measuring the concentration of only stable HbA1c, the value of a ratio of stable HbA1c becomes a low value due to the influence of mutant hemoglobin and minor hemoglobin.

In contrast, in a separation analysis method for separating hemoglobin into various fractions and measuring them, for example, cation exchange chromatography and isoelectric chromatography based on high precision liquid chromatography (HPLC), capillary electrophoresis, gel electrophoresis, and the like, stable HbA1c, glycosylated mutant hemoglobin, glycosylated minor hemoglobin, HbA, mutant hemoglobin, minor hemoglobin, and the like can be separated in some cases. According to those separation analysis methods, there are the following cases: where stable HbA1c can be separated from other hemoglobin components; where stable HbA1c cannot be separated from glycosylated mutant hemoglobin or glycosylated minor hemoglobin; where HbA can be separated from mutant hemoglobin and minor hemoglobin; and where HbA cannot be separated from mutant hemoglobin or minor hemoglobin, depending on the way of separation.

Even in the case where stable HbA1c can be separated from other hemoglobin components, when the concentration of stable HbA is calculated without distinguishing HbA from mutant hemoglobin and minor hemoglobin, the amount of hemoglobin is calculated to be larger, with the result that the ratio of stable HbA1c is calculated to be low by mistake. In order to prevent such a mistake, the correct value of a ratio of stable HbA1c is obtained by calculating the amount of only HbA excluding mutant hemoglobin and minor hemoglobin. As an example of calculation, the ratio of stable HbA1c can be obtained by the following expressions: Stable HbA1c %=Stable HbA1c amount/(Total hemoglobin amount−Mutant hemoglobin amount)×100; and Stable HbA1c %=Stable HbA1c amount/(Total hemoglobin amount−Minor hemoglobin amount)×100. On the other hand, in the case where stable HbA1c cannot be measured separately from glycosylated mutant hemoglobin and glycosylated minor hemoglobin, it is desired to use a total value of HbA, the mutant hemoglobin, and the minor hemoglobin. As an example of calculation, the ratio of stable HbA1c can be obtained by the following expressions: Stable HbA1c %=(Stable HbA1c amount+Glycosylated mutant hemoglobin amount)/(Hemoglobin amount including HbA and mutant hemoglobin)×100; and Stable HbA1c %=(Stable HbA1c amount+Glycosylated minor hemoglobin amount)/(Hemoglobin amount including HbA and minor hemoglobin)×100.

Further, there is a case in which the ratios of minor hemoglobin and mutant hemoglobin with respect to total hemoglobin are sometimes calculated as a measurement value such as mutant hemoglobin % (for example, HbF % and HbS %). However, hemoglobin may not be separated as one peak on each hemoglobin kind basis, and for example, HbA is separated into stable HbA1c, labile HbA1c, and other HbA. In such a case, it is desired that the amounts of respective components derived from HbA be totaled to calculate the amount of HbA, or a value obtained by subtracting the amounts of minor hemoglobin and mutant hemoglobin from the total hemoglobin amount be defined as the amount of HbA. As an example of calculation, the ratio of mutant hemoglobin and the ratio of minor hemoglobin can be obtained by the following expressions: Mutant hemoglobin %=Mutant hemoglobin amount/(Total hemoglobin amount−mutant hemoglobin amount)×100; and Minor hemoglobin %=Minor hemoglobin amount/(Stable HbA1c amount+labile HbA1c amount+HbA0 amount)×100.

Figure 5:
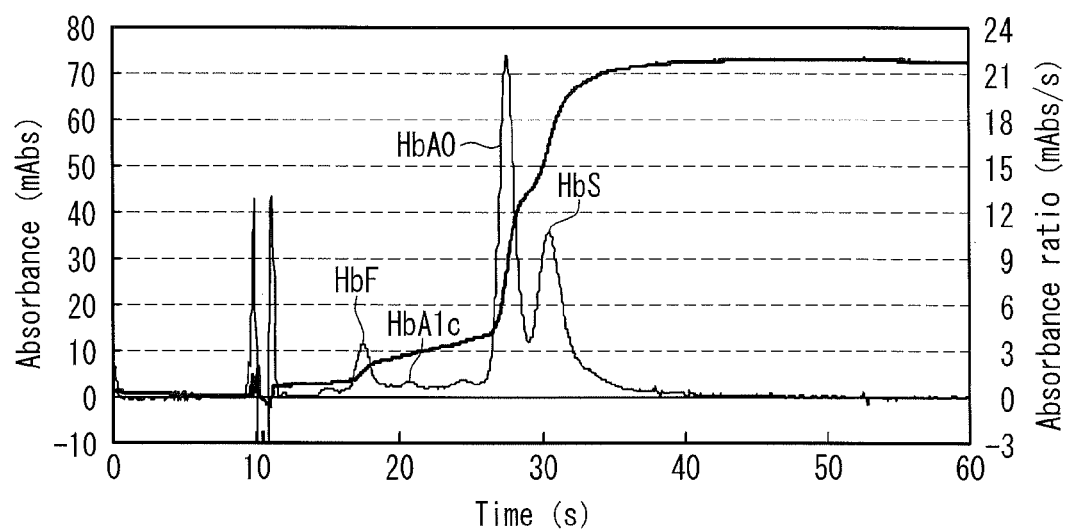
FIG. 5 shows an example of an electroferrogram obtained by capillary electrophoresis using a solution for capillary electrophoresis of Example 3.

As one embodiment, stable HbA1c %, HbF %, and HbA % are calculated from an electroferrogram of FIG. 5. The electroferrogram of FIG. 5 is an example of results obtained by subjecting a sample containing HbF, stable HbA1c, HbA0, and HbS to capillary electrophoresis through use of a solution for capillary electrophoresis in Example 3 described later under the same condition as that of Example 3. The amount of each hemoglobin was as follows. The amount of each hemoglobin was obtained by subtracting an absorbance at the beginning of each peak from an absorbance at the end of each peak. It should be noted that stable HbA1c does not contain glycosylated HbF or glycosylated HbS.

| HbF | 62 |
|---|---|
| Stable HbA1c | 21 |
| HbAO | 349 |
| HbS | 298 |

Stable HbA1c %, HbF %, and HbA % can be calculated as follows.

Stable HbA1c %=21/349×100=6.0%

HbF %=62/(62+21+349+298)=8.5%

HbA %=(21+349)/(62+21+349+298)=50.7%

That is, the present disclosure can relate to one or a plurality of the following embodiments.

[A1] A sample analysis method, including separating and/or detecting a substance to be analyzed in a sample by capillary electrophoresis, wherein the substance to be analyzed is separated and/or detected in a presence of a pH buffer substance and a non-surfactant-type zwitterionic substance.

[A2] A sample analysis method, including:
introducing a sample into a capillary flow path filled with a running buffer solution; and
separating and/or detecting a substance to be analyzed in the sample through capillary electrophoresis by applying a voltage to a whole or a part of the capillary flow path,
wherein the substance to be analyzed is separated and/or detected in a presence of a pH buffer substance and a non-surfactant-type zwitterionic substance.

[A3] The sample analysis method described in [A1] or [A2],
wherein the substance to be analyzed is separated and/or detected in a presence of an ionic pseudostationary phase, the pH buffer substance, and the non-surfactant-type zwitterionic substance.

[A4] The sample analysis method described in any one of [A1] to [A3], wherein the sample contains the pH buffer substance and the non-surfactant-type zwitterionic substance.

[A5] The sample analysis method described in any one of [A1] to [A4], wherein the sample contains an ionic pseudostationary phase, the pH buffer substance, and the non-surfactant-type zwitterionic substance.

[A6] The sample analysis method described in any one of [A1] to [A5], wherein the non-surfactant-type zwitterionic substance is a zwitterionic substance not forming a micelle.

[A7] The sample analysis method described in any one of [A1] to [A6], wherein the non-surfactant-type zwitterionic substance is a substance not having a pH buffering action.

[A8] The sample analysis method described in any one of [A1] to [A7], wherein the non-surfactant-type zwitterionic substance is non-surfactant-type betaine.

[A9] The sample analysis method described in any one of [A1] to [A8], wherein the non-surfactant-type zwitterionic substance is a substance having a quaternary ammonium cation and a sulfo group ($-SO_3^-$) or a carboxyl group ($-COO^-$) at positions not adjacent to each other in the same molecule.

[A10] The sample analysis method described in any one of [A1] to [A9], wherein the pH buffer substance is a substance whose value of pKa or pKb is in a range of ±2.0 of pH under a running condition.

[A11] The sample analysis method described in any one of [A3] to [A10], wherein the ionic pseudostationary phase is an anionic or cationic polymer.

[A12] The sample analysis method described in any one of [A1] to [A11], wherein the sample is a sample containing hemoglobin.

[A13] The sample analysis method described in any one of [A1] to [A12], wherein the sample is capable of containing a substance selected from a group consisting of stable HbA1c (s-HbA1c), hemoglobin A0 (HbA0), hemoglobin A1a (HbA1a), hemoglobin A1b (HbA1b), hemoglobin A1d (HbA1d), hemoglobin A1e (HbA1e), hemoglobin A2 (HbA2), hemoglobin S (HbS, sickle-cell hemoglobin), hemoglobin F (HbF, fetus hemoglobin), hemoglobin M (HbM), hemoglobin C (HbC), hemoglobin D (HbD), hemoglobin E (HbE), methemoglobin, carbamylated hemoglobin, acetylated hemoglobin, aldehyde hemoglobin, and labile HbA1c (l-HbA1c), as a substance to be analyzed.

[A14] The sample analysis method described in any one of [A1] to [A13], wherein a running buffer solution of capillary electrophoresis has a pH of 3.0 to 6.9.

[A15] The sample analysis method described in any one of [A1] to [A14], wherein the ionic pseudostationary phase is a polysaccharide having an anionic group.

[A16] A solution for capillary electrophoresis, including a pH buffer substance, a non-surfactant-type zwitterionic substance, and water.

[A17] The solution for capillary electrophoresis described in [A16], further including an ionic pseudostationary phase.

[A18] The solution for capillary electrophoresis described in any one of [A16] and [A17], wherein the non-surfactant-type zwitterionic substance is a zwitterionic substance not forming a micelle.

[A19] The solution for capillary electrophoresis described in any one of [A16] to [A18], wherein the non-surfactant-type zwitterionic substance is a substance not having a pH buffering action.

[A20] The solution for capillary electrophoresis described in any one of [A16] to [A19], wherein the non-surfactant-type zwitterionic substance is non-surfactant-type betaine.

[A21] The solution for capillary electrophoresis described in any one of [A16] to [A20], wherein the non-surfactant-type zwitterionic substance is a substance containing a quaternary ammonium cation and a sulfo group ($-SO_3^-$) or a carboxyl group ($-COO^-$) at positions not adjacent to each other in the same molecule.

[A22] The solution for capillary electrophoresis described in any one of [A16] to [A21], wherein the pH buffer substance is a substance whose value of pKa or pKb is in a range of ±2.0 of pH under a running condition.

[A23] The solution for capillary electrophoresis described in any one of [A17] to [A22], wherein the ionic pseudostationary phase is an anionic or cationic polymer.

[A24] The solution for capillary electrophoresis described in any one of [A17] to [A23], wherein the ionic pseudostationary phase is a polysaccharide having an anionic group.

[A25] The solution for capillary electrophoresis described in any one of [A16] to [A24], wherein the solution has a pH of 3.0 to 6.9.

[A26] A sample analysis kit, including: the solution for capillary electrophoresis described in any one of [A16] to [A25] and a capillary electrophoresis chip,
wherein the capillary electrophoresis chip includes a sample holding tank, a running buffer solution holding tank, and a capillary flow path, in which the sample holding tank and the running buffer solution holding tank communicate with each other through the capillary flow path.

[A27] The sample analysis kit described in [A26], further including a calibration material and/or a control material.

[A28] A sample analysis method, including:
introducing a sample into a capillary flow path filled with a running buffer solution; and
separating and/or detecting a substance to be analyzed in the sample through capillary electrophoresis by applying a voltage to a whole or a part of the flow path,
the method further including bringing a solution containing an anionic pseudostationary phase and an acid having two or more acid functional groups or a solution containing a weakly basic compound having one basic functional group and a functional group that is likely to be anionic into contact with a capillary whose capillary inner wall is covered with a cationic substance.

EXAMPLES

Hereinafter, the present disclosure is described in more detail by way of examples. It should be noted that the examples are shown merely for illustrative purposes, and the present disclosure is not limited to those examples.

Examples 1 to 4 and Comparative Examples 1 and 2

1. Preparation of Solution for Capillary Electrophoresis

First, 40 mM of citric acid, 1 w/v % of sodium chondroitin sulfate C (produced by Wako Pure Chemical Industries, Ltd.), and 0.1 w/v % of Emulgen SL-110 (produced by Kao Corporation) were mixed, and dimethylaminoethanol was added to the mixture to adjust the pH thereof to 5.3, whereby a solution for capillary electrophoresis of Comparative Example 1 was prepared (Table 1).

Then, NDSB-201 (3-(1-Pyridino)-1-propane sulfonate, non-surfactant-type sulfobetaine, produced by Affymetrix, Inc.) was added to the solution for capillary electrophoresis of Comparative Example 1 so that the final concentration of the NDSB-201 became 500 mM and 250 mM, whereby solutions for capillary electrophoresis of Examples 1 and 2 were respectively prepared (Table 1). Further, the same solution for capillary electrophoresis as that of Comparative Example 1 was prepared as a solution for capillary electrophoresis of Comparative Example 2. Then, betaine (trimethylglycine, non-surfactant-type betaine, produced by Wako Pure Chemical Industries, Ltd.) was added to the solution for capillary electrophoresis of Comparative Example 2 so that the final concentration of the betaine became 500 mM, whereby a solution for capillary electrophoresis of Example 3 was prepared. Further, NDSB-211 (Dimethyl(2-hydroxyethyl)ammonium propane sulfonate, non-surfactant-type sulfobetaine, produced by Affymetrix, Inc.) was added to the solution for capillary electrophoresis of Comparative Example 2 so that the final concentration of the NDSB-211 became 250 mM, whereby a solution for capillary electrophoresis of Example 4 was prepared (Table 2).

2. Provision of Sample Raw Material

Whole blood of a healthy person collected through use of a blood-collecting vessel containing an anticoagulant was defined as a sample raw material.

3. Separation Device (Capillary Electrophoresis Chip)

As a capillary electrophoresis chip for sample analysis, a capillary electrophoresis chip 1 shown in FIG. 1 was used. A capillary electrophoresis chip 1 shown in FIG. 1 is configured in such a manner that an upper substrate 2a is stacked on a lower substrate 2b. The upper substrate 2a is provided with two through-holes, and the two through-holes are sealed with the lower substrate 2b to form a sample holding tank 4 and a running buffer solution holding tank 5. The lower substrate 2b is provided with an I-shaped groove, and the upper substrate 2a is stacked on an upper part of the groove to form a capillary flow path 3. The sample holding tank 4 and the running buffer solution holding tank 5 communicate with each other through the capillary flow path 3. The capillary flow path 3 has a cross-section area of 0.04×0.04 mm, and the distance between the sample holding tank 4 and the running buffer solution holding tank 5 is 30 mm. A detection section 6 is disposed at a position of 20 mm from the sample holding tank 4 and 10 mm from the running buffer solution holding tank 5.

[Production of Capillary Electrophoresis Chips A and B]

A capillary electrophoresis chip A was produced as follows. Protein (hemoglobin) was allowed to adsorb to the capillary flow path 3 of the capillary electrophoresis chip 1, and the capillary flow path 3 was further coated with chondroitin sulfate. Specifically, the capillary flow path 3 was filled with a hemoglobin solution to allow the hemoglobin solution to hydrophobically adsorb to the capillary flow path 3, and thereafter, a solution (pH 5.3) containing 40 mM of citric acid and 1 w/v % of chondroitin sulfate was passed through the capillary flow path 3 to coat the capillary flow path 3 with the solution.

A capillary electrophoresis chip B was produced as follows. The capillary flow path 3 of the capillary electrophoresis chip 1 was treated with a silane coupling agent (3-aminopropyltrimethoxysilane) so as to introduce an amino group into the capillary flow path 3, and further, the capillary flow path 3 was coated with chondroitin sulfate. Specifically, a solution (pH 5.3) containing 40 mM of citric acid and 1 w/v % of chondroitin sulfate was passed through the capillary flow path 3 to coat the capillary flow path 3 with the solution.

4. Capillary Electrophoresis

Capillary electrophoresis was performed under the following running condition A through use of the solutions for capillary electrophoresis of Examples 1, 2 and Comparative Example 1 and the capillary electrophoresis chip A. Further, capillary electrophoresis was performed under the following running condition B through use of the solutions for capillary electrophoresis of Examples 3, 4 and Comparative Example 2 and the capillary electrophoresis chip B. FIGS. 2A to 2C and 3A to 3C show electropherrograms thus obtained, and Tables 2 and 3 show relative values of measured average current values. It should be noted that the average current value is calculated by averaging current values between electrodes from the beginning of electrohporesis to the end thereof.

[Measurement Device]

Capillary electrophoresis of the capillary electrophoresis chip 1 was performed through use of an apparatus produced by ARKRAY, Inc. In the detection section 6 of the capillary electrophoresis chip 1, an absorbance at a wavelength of 415 nm was measured. An absorbance was measured continuously at an interval of 0.02 seconds from the beginning of electrophoresis to the end thereof.

[Running Condition A]

1: First, 9 µL of each solution for capillary electrophoresis of Comparative Example 1 is added to the running buffer solution holding tank 5 on the capillary electrophoresis chip A to fill the capillary flow path 3 with each solution for capillary electrophoresis of Comparative Example 1.

2: Next, 9 µL of a sample prepared by diluting a sample raw material by 25 times with each solution for capillary electrophoresis of Examples 1, 2 and Comparative Example 1 is added to the sample holding tank 4 on the capillary electrophoresis chip A.

3: Next, a positive electrode and a negative electrode are brought into contact with the sample holding tank 4 and the running buffer solution holding tank 5, respectively, and a voltage of 1,800 V is applied between the sample holding tank 4 and the running buffer solution holding tank 5 to start electrophoresis.

4: An absorbance at a wavelength of 415 nm is measured in the detection section 6 to obtain an electropherrogram.

Further, during the application of a voltage, a current value is measured. Electrophoresis is performed for 90 seconds.
[Running Condition B]

1: First, 9 µL of each solution for capillary electrophoresis of Comparative Example 2 is added to the running buffer solution holding tank 5 on the capillary electrophoresis chip B to fill the capillary flow path 3 with each solution for capillary electrophoresis of Comparative Example 2.

2: Next, 9 µL of a sample prepared by diluting a sample raw material by 25 times with each solution for capillary electrophoresis of Examples 3, 4 and Comparative Example 2 is added to the sample holding tank 4 on the capillary electrophoresis chip B.

3: Next, a positive electrode and a negative electrode are brought into contact with the sample holding tank 4 and the running buffer solution holding tank 5, respectively, and a voltage of 1,800 V is applied between the sample holding tank 4 and the running buffer solution holding tank 5 to start electrophoresis.

4: An absorbance at a wavelength of 415 nm is measured in the detection section 6 to obtain an electropherrogram. Further, during the application of a voltage, a current value is measured. Electrophoresis is performed for 90 seconds.

Comparative Example 2. In this case, an increase in current value during electrophoresis was suppressed in Examples 3 and 4, compared with that of Comparative Example 2 (Table 2).

The capillary electrophoresis chips A and B have different inner wall treatment conditions of the capillary flow path 3, but have the effects such as shortening of measurement time and suppression of an increase in current value in common. Further, Examples 1 to 4 use different non-surfactant-type zwitterionic substances, but have the effects of shortening of measurement time and suppression of an increase in current value in common.

Example 5 and Comparative Examples 3 to 4

1. Preparation of Solution for Capillary Electrophoresis

A solution for capillary electrophoresis of Comparative Example 3 was prepared in the same way as in Comparative Example 1.

NDSB-201 was added to the solution for capillary electrophoresis of Comparative Example 3 so that the final

TABLE 1

|  | pH buffer substance (40 mM) | Ionic pseudostationary phase (0.1% by weight) | pH | Non-surfactant-type zwitterionic substance | Capillary electrophoresis chip | Average current value (relative value) |
| --- | --- | --- | --- | --- | --- | --- |
| Example 1 | Citric acid | sodium chondroitin sulfate C | 5.3 | NDSB-201 500 mM | A | 85.16 |
| Example 2 | Citric acid | sodium chondroitin sulfate C | 5.3 | NDSB-201 250 mM | A | 93.97 |
| Comparative Example 1 | Citric acid | sodium chondroitin sulfate C | 5.3 | None | A | 100.00 |

TABLE 2

|  | pH buffer substance (40 mM) | Ionic pseudostationary phase (0.1% by weight) | pH | Non-surfactant-type zwitterionic substance | Capillary electrophoresis chip | Average current value (relative value) |
| --- | --- | --- | --- | --- | --- | --- |
| Example 3 | Citric acid | sodium chondroitin sulfate C | 5.3 | betaine 500 mM | B | 86.85 |
| Example 4 | Citric acid | sodium chondroitin sulfate C | 5.3 | NDSB-211 250 mM | B | 99.46 |
| Comparative Example 2 | Citric acid | sodium chondroitin sulfate C | 5.3 | None | B | 100.00 |

It is understood from FIGS. 2 and 3 that, in Examples 1 to 4 in which a sample was prepared with a solution for capillary electrophoresis having a non-surfactant-type zwitterionic substance added thereto and used, detection time was shortened compared with Comparative Examples 1 and 2 in which the non-surfactant-type zwitterionic substance was not added.

Further, as shown in FIG. 2, methemoglobin was detected in Comparative Example 1, whereas the generation of methemoglobin was suppressed in Examples 1 and 2. In this case, an increase in current value during electrophoresis was suppressed in Examples 1 and 2, compared with that of Comparative Example 1.

Further, as shown in FIG. 3, an increase in peak width was suppressed in Examples 3 and 4, compared with that of concentration of the NDSB-201 became 250 mM to prepare a solution for capillary electrophoresis of Example 5 (same as Example 2). Further, palmitylsulfobetaine (SB3-16 (trade name) produced by Tokyo Ohka Kogyo Co., Ltd.) was added to the solution for capillary electrophoresis of Comparative Example 5 so that the final concentration of the palmitylsulfobetaine became 1.0 v/v % to prepare a solution for capillary electrophoresis of Comparative Example 4.

2. Sample Raw Material and Separation Device

The above-mentioned whole blood was used as a sample raw material. As a capillary electrophoresis chip, the capillary electrophoresis chip B was used.

3. Capillary Electrophoresis

Capillary electrophoresis was performed under the following condition C through use of the solutions for capillary electrophoresis of Example 5 and Comparative Examples 3, 4 and the capillary electrophoresis chip B. FIGS. 2A to 2C and 3A to 3C show electropherrograms thus obtained, and Table 4 show relative values of measured average current values.

[Measurement Device]

Capillary electrophoresis of a capillary electrophoresis chip was performed through use of the same apparatus as described above.

[Running Condition C]

1: First, 9 μL of each solution for capillary electrophoresis of Example 5 and Comparative Examples 3, 4 is added to the running buffer solution holding tank 5 on the capillary electrophoresis chip B to fill the capillary flow path 3 with each solution for capillary electrophoresis of Example 5 and Comparative Examples 3, 4.

2: Next, 9 μL of a sample prepared by diluting a sample raw material by 25 times with each solution for capillary electrophoresis of Example 5 and Comparative Examples 3, 4 is added to the sample holding tank 4 on the capillary electrophoresis chip B.

3: Next, a positive electrode and a negative electrode are brought into contact with the sample holding tank 4 and the running buffer solution holding tank 5, respectively, and a voltage of 1,600 V is applied between the sample holding tank 4 and the running buffer solution holding tank 5 to start electrophoresis.

4: An absorbance at a wavelength of 415 nm is measured in the detection section 6 to obtain an electropherrogram. Further, during the application of a voltage, a current value is measured. Electrophoresis is performed for 60 seconds.

TABLE 3

|  | pH buffer substance (40 mM) | Ionic pseudostationary phase (0.1% by weight) | pH | Non-surfactant-type zwitterionic substance | Capillary electrophoresis chip | Average current value (relative value) |
|---|---|---|---|---|---|---|
| Example 5 | Citric acid | sodium chondroitin sulfate C | 5.3 | NDSB-201 250 mM | B | 95.52 |
| Comparative Example 3 | Citric acid | sodium chondroitin sulfate C | 5.3 | None | B | 100.00 |
| Comparative Example 4 | Citric acid | sodium chondroitin sulfate C | 5.3 | Surfactant type sulfobetaine 1 v/v % | B | 95.93 |

Figure 4A:
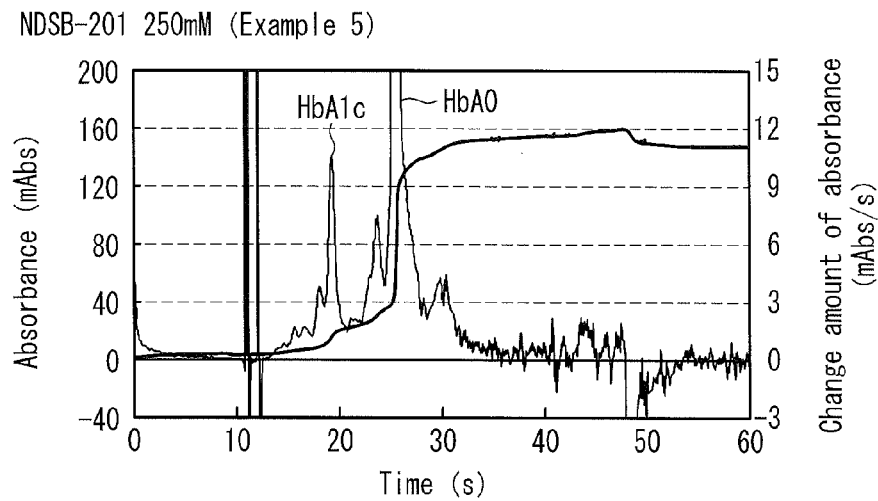
FIG. 4A shows an example of an electroferrogram obtained by capillary electrophoresis using a solution for capillary electrophoresis of Example 5.
Figure 4B:
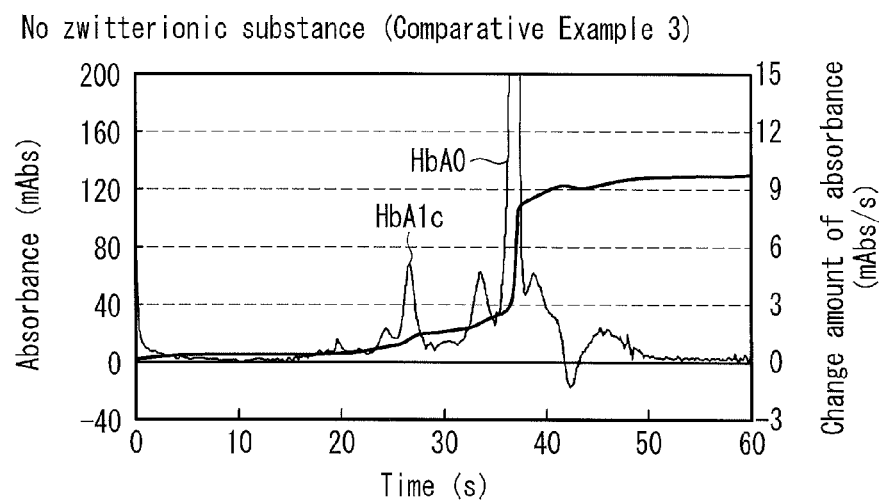
FIG. 4B shows an example of an electroferrogram obtained by capillary electrophoresis using a solution for capillary electrophoresis of Comparative Example 3.
Figure 4C:
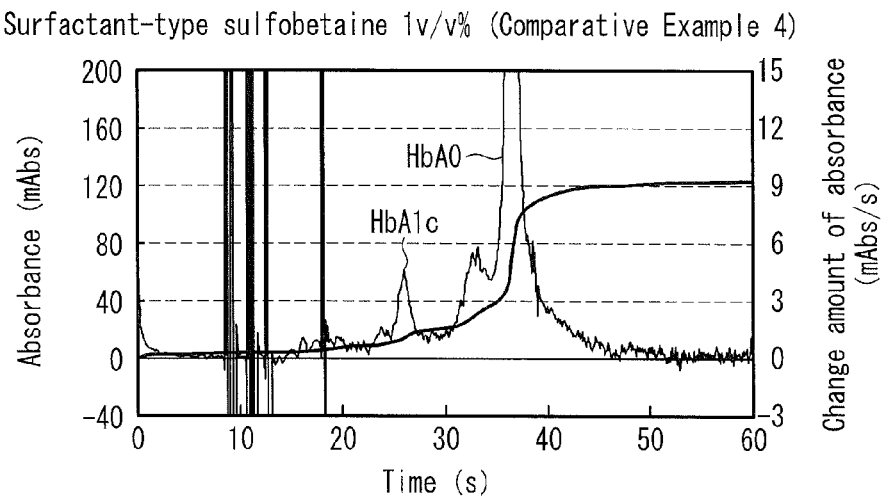
FIG. 4C shows an example of an electroferrogram obtained by capillary electrophoresis using a solution for capillary electrophoresis of Comparative Example 4.

It was confirmed from the results of Example 5 shown in Table 3 and FIG. 4 that effects such as suppression of a current value and shortening of analysis time can be obtained even in the case where a non-surfactant-type zwitterionic substance is present in the capillary flow path 3 before the beginning of running.

Further, it was confirmed from the results of Comparative Example 4 shown in Table 3 and FIG. 4 that there is an effect of suppression of a current value whereas there is no effect of shortening of analysis time in the case where a surfactant-type zwitterionic substance is used in place of a non-surfactant-type zwitterionic substance.

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes which come within the meaning and range of equivalency of the claims are intended to be embraced therein.

What is claimed is:

1. A sample analysis method, comprising:
   separating and/or detecting a substance to be analyzed in a sample by capillary electrophoresis in the presence of a running buffer,
   wherein the sample comprises hemoglobin, and
   the running buffer has a pH of 3.0 to 6.9 and comprises an ionic pseudostationary phase, a pH buffer substance and a non-surfactant-type zwitterionic substance, where the non-surfactant-type zwitterionic substance is a non-surfactant-type betaine.

2. The sample analysis method according to claim 1, further comprising:
   introducing the sample into a capillary flow path filled with the running buffer solution; and
   separating and/or detecting the substance to be analyzed through capillary electrophoresis by applying a voltage to a whole or to a part of the capillary flow path.

3. The sample analysis method according to claim 1, wherein the sample further comprises the pH buffer substance and the non-surfactant-type zwitterionic substance.

4. The sample analysis method according to claim 1, wherein the sample further comprises the ionic pseudostationary phase, the pH buffer substance, and the non-surfactant-type zwitterionic substance.

5. The sample analysis method according to claim 1, wherein the non-surfactant-type zwitterionic substance does not form a micelle.

6. The sample analysis method according to claim 1, wherein the non-surfactant-type zwitterionic substance has a quaternary ammonium cation and either a sulfo group ($—SO_3^-$) or a carboxyl group ($—COO^-$) at positions not adjacent to each other in the same molecule.

7. The sample analysis method according to claim 1, wherein the pH buffer substance has a pKa or pKb in a pH range of ±2.0 under running conditions.

8. The sample analysis method according to claim 1, wherein the ionic pseudostationary phase is an anionic or a cationic polymer.

9. The sample analysis method according to claim 1, wherein the substance to be analyzed is selected from the group consisting of stable HbA1c (s-HbA1c), hemoglobin A0 (HbA0), hemoglobin A1a (HbA1a), hemoglobin A1b (HbA1b), hemoglobin A1d (HbA1d), hemoglobin A1e (HbA1e), hemoglobin A2 (HbA2), hemoglobin S (HbS, sickle-cell hemoglobin), hemoglobin F (HbF, fetus hemoglobin), hemoglobin M (HbM), hemoglobin C (HbC), hemoglobin D (HbD), hemoglobin E (HbE), methemoglobin, carbamylated hemoglobin, acetylated hemoglobin, aldehyde hemoglobin, and labile HbA1c (l-HbA1c).

10. The sample analysis method according to claim 1, wherein the running buffer solution has a pH of 3.0 to 6.0.

11. The sample analysis method according to claim 1, wherein the ionic pseudostationary phase is a polysaccharide having an anionic group.

\* \* \* \* \*